United States Patent [19]
Murthy et al.

[11] Patent Number: 5,998,616
[45] Date of Patent: *Dec. 7, 1999

[54] BIOCATALYST FOR THE CONVERSION OF CARBONYL COMPOUNDS TO THEIR β-UNSATURATED DERIVATIVES USING MOLECULAR OXYGEN AS THE OXIDANT

[75] Inventors: Yerramilli V. S. N. Murthy; Vincent Massey, both of Ann Arbor, Mich.

[73] Assignee: The University of Michigan, Ann Arbor, Mich.

[*] Notice: This patent issued on a continued prosecution application filed under 37 CFR 1.53(d), and is subject to the twenty year patent term provisions of 35 U.S.C. 154(a)(2).

[21] Appl. No.: 08/920,228

[22] Filed: Aug. 25, 1997

[51] Int. Cl.$^6$ .................................................. C07D 475/00
[52] U.S. Cl. ........................... 544/257; 436/518; 536/529
[58] Field of Search .................................... 544/243, 257; 436/518; 536/529

[56] References Cited

U.S. PATENT DOCUMENTS 4,298,735   11/1981   Farina et al. ............................. 544/257

OTHER PUBLICATIONS

Murthy et al., "Syntheses and Applications of Flavine Analogs as Active Site Probes for Flavoproteins", Methods in Enzymology, vol. 280, 1997, pp. 436–460.

Murthy & Massey "Synthesis And Properties Of 8–CN–Flavins And Reconstituted Flavoproteins," Yerramilli V.S.N. Murthy & Vincent Massey, Department of Biological Chemistry, University of Michigan, Ann Arbor, MI, Abstract No. 046, 212$^{th}$ ACS National Meeting, mailed to public Aug. 8, 1996.

*Primary Examiner*—Mukund J. Shah
*Assistant Examiner*—Pavanaram K Sripada
*Attorney, Agent, or Firm*—Brinks Hofer Gilson & Lione

[57] ABSTRACT

The present invention provides a general biocatalyst for transforming saturated carbonyl compounds to their α,β-unsaturated analogs. The transformation is regio- as well as stereoselective. These catalysts are useful in the chiral resolution of carbonyl compounds as well as in the development of libraries of small molecules to screen as potential drug candidates.

5 Claims, No Drawings

BIOCATALYST FOR THE CONVERSION OF CARBONYL COMPOUNDS TO THEIR β-UNSATURATED DERIVATIVES USING MOLECULAR OXYGEN AS THE OXIDANT

The U.S. Government has certain rights in this invention pursuant to Grant Nos. NIH-GIM11106 and NSF-MCB 9313781, awarded by the National Institutes of Health and the National Science Foundation, respectively.

BACKGROUND OF THE INVENTION

1. Field of the Invention

The present invention provides a novel catalyst for transforming saturated carbonyl compounds to their α,β-unsaturated analogs. The invention also provides a process for producing ,β-unsaturated carbonyl compounds using this catalyst.

2. Background of the Invention

The ,β-unsaturated ketone functionality enjoys a unique position in organic chemistry. It is used in a diverse array of reactions, including 1,2- or 1,4-additions, alkylations, Diels-Alder reactions, and has played a pivotal role in many syntheses of complex molecules in racemic or optically active form. However, the utility of this class of compounds is limited by the difficulty of obtaining them. That is, it is difficult to selectively catalyze the oxidation of simple carbonyl precursors directly to their corresponding ,β-unsaturated derivatives (enones) under mild conditions.

Although a few reports exist for isolated reactions that yield specific compounds, to date no general catalysts or methods are believed to be available to carry out this important transformation. Further, the existing reactions are plagued by low yields and lack of regioselectivity when the reaction involves an unsymmetric carbonyl compound. Also, the conventional catalysts are generally highly toxic, pyrophoric and "environmentally unfriendly," often resulting in harmful byproducts.

Accordingly, a catalyst which oxidizes a carbonyl-containing compounds into their corresponding ,β-unsaturated derivatives under mild conditions is desirable.

SUMMARY OF THE INVENTION

Accordingly, this invention provides a process for oxidizing saturated carbonyl-containing compounds to their corresponding ,β-unsaturated derivatives under mild conditions.

This invention also provides an enviromentally friendly catalytic system that converts saturated carbonyl containing compounds to their corresponding ,β-unsaturated derivatives chemoselectively, regioselectively and enantioselectively.

Finally, this invention utilizes the advantages of an immobilized catalyst.

Specifically, the present inventors discovered that complexes of a flavoprotein containing derivatives of the cofactor flavinmononucleotide (FMN) oxidize saturated carbonyl-containing compounds to their corresponding ,β-unsaturated derivatives under mild conditions.

BRIEF DESCRIPTION OF THE DRAWINGS

FIG. 1 is a Table illustrating the wide range of substrates accepted by the catalytic system of the present invention.

DETAILED DESCRIPTION OF EMBODIMENTS

This invention is a method of oxidizing reducing carbonyl-containing compounds into their corresponding ,β-unsaturated derivatives. The oxidation reaction consists of contacting a substrate (carbonyl-containing compounds) in an oxygen containing solution with a catalytic system, and sampling the solution to determine the concentrations of product and remaining substrate.

Catalytic System

The catalytic system comprises a cofactor bound to an enzyme. The system can be either soluble or immobilized. "Bound to" means that the cofactor and enzyme coordinate or form a complex. Preferably, the binding affinity of the cofactor to the enzyme is at least about 10 nM.

Cofactor

Suitable cofactors useful in the present invention are derivatives of flavin mononucleotide (FMN), which has the structure:

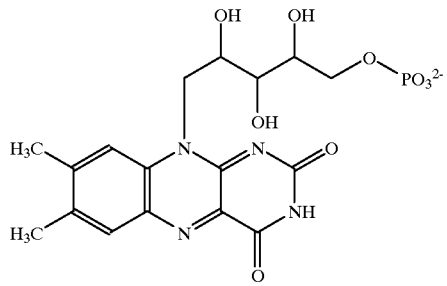

The cofactor of the present invention is a derivative of the formula (I):

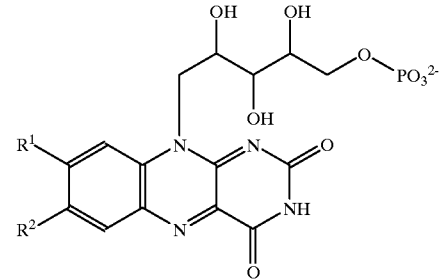

where $R^1$ is —CN or —COOR, $R^2$ is $C_{1-6}$ alkyl, preferably methyl.

The cofactors of the present invention have redox potentials which are at least about 50 mV, preferably about 100 mV, more positive than the native cofactor, FMN, when bound to Old Yellow Enzyme.

In a preferred flavin cofactor of the formula (I), $R^1$ is —CN and $R^2$ is methyl, as shown below.

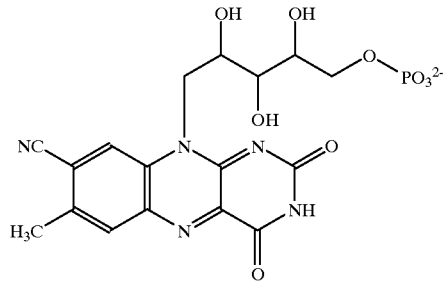

The redox potential of this preferred flavin cofactor is −38 mV, which is about 170 mV positive to the native cofactor, FMN. The above cofactor is referred to hereinafter as 8-CN-FMN. When bound to an enzyme, such as Old Yellow Enzyme, the complex is referred to as 8-CN-FMN-OYE.

Enzyme

The enzyme used in the oxidation reaction of the present invention is any flavoprotein that can reduce ,β-unsaturated carbonyl compounds to their saturated analogs. Suitable flavoproteins include Old Yellow Enzyme and acyl coenzyme A dehydrogenase. Preferably, Old Yellow Enzyme is used.

Old Yellow Enzyme can be obtained from Brewer's Bottom Yeast. Recombinant forms of the enzyme can also be used and obtained using conventional cloning techniques. This enzyme is very stable to the reaction of the present invention, retaining its activity even after several thousand turnovers.

Substrates

The process of the invention is general in scope, that is to say, it is usable for a wide range of saturated carbonyl-containing compounds. Table 1 shows a range of substrates which have been oxidized using the cofactor of the present invention. Useful substrates include aldehydes, ketones, lactones, amides, including heterocyclic substrates like cyclic amides and cyclic lactones.

Suitable substrates containing saturated aldehyde groups include compounds of the formula:

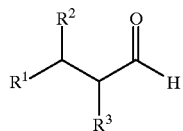

where $R^1$ is hydrogen, amino, $C_{1-20}$ dialkylamino, $C_{1-20}$ aminoalkyl, $C_{1-20}$ diaminoalkyl, halogen, $C_{1-20}$ alkyl, $C_{2-20}$ alkenyl, $C_{1-20}$ alkyloxy, $C_{6-20}$ aralkyl, $C_{6-10}$ aryl, $C_{5-10}$ heterocyclic ring;

$R^2$ is hydrogen, halogen, $C_{1-20}$ alkyl; and $R^3$ is hydrogen, halogen, $C_{1-20}$ alkyl; or $R^2$ and $R^3$ together form a $C_{5-8}$ cycloalkyl, $C_{6-10}$ aryl, $C_{5-10}$ heterocyclic ring or a fused ring system containing 10–20 atoms.

Suitable substrates containing saturated ketone groups include compounds of the formula:

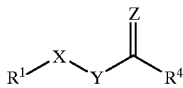

where $R^4$ is amino, $C_{1-20}$ dialkylamnino, $C_{1-20}$ aminoalkyl, $C_{1-20}$ diaminoalkyl, halogen, $C_{1-20}$ alkyl, $C_{2-20}$ alkenyl, $C_{1-20}$ alkyloxy, $C_{1-20}$ alkylthiol, $C_{6-20}$ aralkyl, $C_{6-10}$ aryl, $C_{5-10}$ heterocyclic ring, $C_{1-20}$ hydroxyalkyl, and $C_{1-20}$ thioalkyl;

X is NH or $CHR^2$;

Y is NH or $CHR^3$;

Z is O or S; and $R^1$, $R^2$ and $R^3$ are as described above.

Suitable cyclic substrates include compounds of the formula:

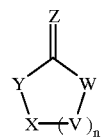

where n is 0–4;

V is $CH_2$, $CHR^1$; $CR^1_2$;

W is O, CH, NH, or S;

X is NH or $CHR^5$;

Y is NH or $CHR^6$;

Z is S or O;

$R^1$ is as described above;

$R^5$ is $C_{1-20}$ alkyl, $C_{2-20}$ alkenyl, $C_{1-20}$ alkyloxy, $C_{6-20}$ aralkyl, $C_{6-10}$ aryl, $C_{5-10}$ heterocyclic ring; and $R^6$ is $C_{1-20}$ alkyl, $C_{2-20}$ alkenyl, $C_{1-20}$ alkyloxy, $C_{6-20}$ aralkyl, $C_{6-10}$ aryl, $C_{5-10}$ heterocyclic ring; or $R^5$ and $R^6$ together form a $C_{5-8}$ cycloalkyl, $C_{6-10}$ aryl, $C_{5-10}$ heterocyclic ring or a fused ring system containing 10–20 atoms.

Acyl includes conventional groups derived, for example, from carboxylic, carbonic, sulfonic and carbamic acids. Preferred acyl groups include lower alkanoyl (e.g. formyl, acetyl, propionyl, butyryl, isobutyryl, valeryl, isovaleryl, pivaloyl, hexanoyl, etc.), lower alkanesulfonyl (e.g. mesyl, ethanesulfonyl, propanesulfonyl, etc.). These acyl groups may be substituted with suitable substituent(s) such as halogen (e.g. chlorine, bromine, iodine, fluorine).

Alkyl includes straight or branched chain, aliphatic or cyclic, alkyl groups having 1 to 20 carbon atom(s). Preferred alkyl groups have 1–6 carbon atoms, including methyl, ethyl, propyl, isopropyl, butyl, t-butyl, pentyl, hexyl. The most preferred one is methyl, ethyl or propyl.

Alkenyl includes straight or branched chain, aliphatic or cyclic, alkyl groups having at least one double bond therein. Preferred alkenyl groups include vinyl, 1-propenyl, allyl, 1-butenyl, 2-butenyl, 2-pentenyl.

Aryl includes xylenes, $C_{1-6}$ alkylbenzenes, $C_{1-6}$ alkoxybenzenes, naphthalene, anthracene, phenanthrene and higher condensed aromatics, phenol, hydroquinone, resorcinol, catechol, pyrogallol, biphenyl, and the like preferably phenyl. The aryl groups can be unsubstituted or substituted with 1–4 substituents selected from the group consisting of $C_{1-6}$ alkyl, nitro, carboxyl, carboxy-$C_{1-6}$ alkyl, $C_{1-4}$ acyl, cyano, $C_{1-6}$ alkoxy and halogen.

Halogen includes fluoro, chloro, bromo and iodo, preferably chloro.

Heterocyclic groups include 5 to 8 membered alkyl ring systems in which one or more carbon atoms is replaced by a nitrogen, sulphur or oxygen atoms. Preferred heterocyclic groups include morpholino, quinolinyl, isoquinolinyl, pyrridinyl, indolinyl, furanyl, thiazonyl, phenanthrolinyl, phenanthridinyl and furfural. The heterocyclic groups can be unsubstituted or substituted with 1–4 substituents selected from the group consisting of $C_{1-20}$ alky, nitro, carboxyl, carboxy-$C_{1-6}$ alkyl, $C_{1-4}$ acyl, cyano, $C_{1-6}$ alkoxy and halogen.

Reaction Conditions

The reaction consists of contacting the substrate in an oxygen containing solution with a catalytic system comprising the cofactor bound to the enzyme, and isolating the product from the solution. The process can also include an additional step of sampling the solution to determine the concentrations of product and remaining substrate, prior to the isolating step.

The products result from a regio-, stereo- and entantio-specific oxidation.

The oxidant is molecular oxygen, conveniently in the form of air. As the reaction rate is proportional to the concentration of oxygen, bubbling $O_2$ gas through the reaction mixture can increase the efficiency of the reaction.

The oxidation may be detected by absorbence spectroscopy, by following the formation of product at wavelengths specific for the compound being oxidized.

The reaction is typically conducted in an aqueous buffer solution. Preferred electrolytic solutions include monobasic or dibasic phosphate buffer solutions ($MHPO_4$ or $M_2PO_4$, where M is an alkali or alkaline metal salt such as $Na^+$ or $K^+$) or mixtures thereof These electrolyte solutions are prepared from distilled water and salts of high purity. Typically, the molarity of the electrolytic solutions are about 0.5 to 0.05 M, preferably about 0.1 M. A mixed solvent system containing water and an organic solvent can also be used. For example, a mixture of up to about 35% alcohol (such as methanol) and about 65% aqueous buffer solutions can be used without loss of activity.

The working conditions, temperature and pH, of the process of the invention are closely linked to the main synthetic reaction, providing for the latter the stability of the enzymes and a maximal yield. The reaction is typically conducted for about 180 minutes, although the time can be extended. The temperature will generally be between about 0° C. and 40° C., preferably about 25° C. The pH between about 7 and 10.

In an alternate embodiment, the enzyme can be immobilized on a solid support. For example, the enzyme can be immobilized on an insoluble polymer support such as on 6-aminohexanoicacid N-hydroxysuccinimide estersepharose 4B. In this manner, the enzyme can be recovered from the reaction mixture by simple filtration.

EXAMPLES

Synthesis of 8-CN-riboflavin 10 mg of 8-amino-riboflavin (Berezovskii, V. M., Tulchinskaya, L. S., & Polyankova, N. A. zh-Obshch-Khim (1965) (675–681) was suspended in 3 ml of water in a test tube. To this suspension, 6N HCl was added till a clear solution was obtained. This solution was cooled to 0° C. on ice and 3 aliquots each of 40 μl of saturated sodium nitrite solution were added with continuous shaking of the test tube. After 5 minutes, 300 μl of saturated urea solution was added to destroy the excess sodium nitrite. The cold diazo salt solution was then added with a glass transfer pipette to a 10 ml saturated solution of NaCN+CuCN (70:30) in a 50 ml glass beaker with vigorous stirring at room temperature. After 20 minutes, the reaction mixture was loaded on a 20cc C-18 Sep Pak cartridge. The cartridge was prewashed thoroughly with excess water, methanol and again with water before loading the reaction mixture. The Sep Pak cartridge was eluted with water followed by 5% acetonitrile to remove salts and a red band of unknown structure. Elution with 15% acetonitrile gave the 8-CN-riboflavin and with 20% acetonitrile gave 8-Cl-riboflavin. Evaporation of the flavin solutions with a Speed Vac concentrator gave 6 mg of the 8-CN-riboflavin as a yellow powder.

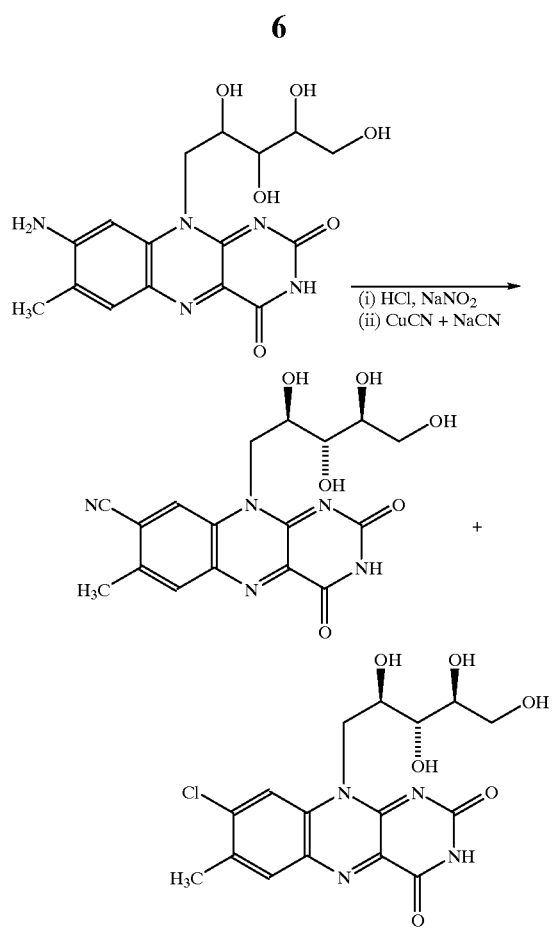

Chemical synthesis of 8-CN-8-Demethyl-Flavinmononucleo (8-CN-FMN)

A small two-necked round bottom flask was sealed with rubber septa and equipped with two needles, one of which is an inlet and the other an outlet for continuous flushing of nitrogen gas. 750 μl of phosphorous oxychloride was introduced from a syringe and cooled at 0° C. After 15 minutes, 292 μl of water was introduced dropwise with vigorous stirring. After the mixture was homogeneous, 12 mg of solid 8-CN-riboflavin was added slowly by opening one of the septa. After the addition, the flask was sealed again with the septum and the flushing with nitrogen stopped. The reaction mixture was stirred overnight and protected from light. The unreacted reagent was hydrolyzed by the careful addition of water (around 2 ml). The solid unreacted 8-CN-riboflavin form was filtered off and aqueous layer was purified over a Sep Pak C-18 cartridge. The fraction obtained by the elution of the cartridge with 5% acetonitrile was evaporated to dryness under vacuum by using a Speed Vac centrifuge and contained mostly the FMN derivative.

Enzymatic conversion of 8-CN-riboflavin to FMN

8-CN-riboflavin was converted to the FAD level with partially purified FAD synthetase from Brevibacterium ammoniagenes by incubating the flavin in 0.002 M Kpi, pH 7.5 at 25° C., following the procedure of Spencer et al. (Biochemistry 1976, 15: 1043–1053) After 14 hours, HPLC analysis of the incubation mixture showed 100% conversion to the FAD form. The reaction mixture was loaded on to the prewashed (as described in the case of 8-CN-riboflavin) 20cc C-18 Sep Pak cartridge and eluted with 100 ml of water to wash off salts, etc. Elution with 5% acetonitrile in water gave pure flavin which was concentrated on a Speed Vac concentrator to obtain 8-CN-FAD as a yellow powder.

8-CN-FMN was obtained by hydrolysis of the FAD in 0.05M Kpi, pH 7, with snake venom phosphodiesterase (Naja naja venom).

Preparation of Old Yellow Enzyme and its apoprotein

Old Yellow Enzyme was isolated from Brewer's Bottom Yeast (Abramovitz, A. S. & Massey, V., J. Biol. Chem. 1976, 251: 5321–5326; Abramovitz, A. S. & Massey, V., J. Biol. Chem. 1976, 251: 5327–5336). OYE I was overexpressed in *Escherichia coli* containing the plasmid pET-3b (Saito, K., Thiele, D. J., Davio, M., Lockridge, O., & Massey, V., J. Biol. Chem. 1991, 266: 20720–20724). The apoOYE-I was prepared from the recombinant enzyme by using the procedure reported for the enzyme from Brewer's Bottom Yeast (Abramovitz, A. S. & Massey, V., J. Biol. Chem. 1976, 251: 5321–5326; Abramovitz, A. S. & Massey, V., J. Biol. Chem. 1976, 251: 5327–5336).

Reconstitution of apoOYE

Reconstitution of the apoOYE with 8-CN-FMN was accomplished by mixing 1.5 fold excess of the flavin with apoprotein and incubating on ice for 3 hours. Excess flavin was removed by a Centricon-30 microconcentrator (Amicon).

8CN-FMN-OYE

The apoprotein of Old Yellow Enzyme was prepared and reconstituted with 8-CN-8-demethyl-flavin mononucleotide as described above. The high potential of the bound flavin was established by forming a phenol complex which showed a charge transfer band with the maximum located at 763 nm. Native enzyme binds p-Cl-phenol with a Kd of ~1 $\mu$M and has a maximum of 645 nm for the charge transfer absorption band. The 115 nm blue shift thus falls in line with the 170 mV more positive potential compared to that of the native flavin.

A typical Reaction Procedure for the Oxidation

Two ml of 10 mM solution of hydrocinnamaldehyde ($C_6H_5$—$CH_2$—$CH_2$—CHO) in 100 mM sodium pyrophosphate buffer, pH 8.5 was taken in a 5 ml test tube with a small magnetic stir bar at room temperature. The catalyst, as a concentrated solution in the same buffer, was added to the above solution so that final concentration of the catalyst is 10 $\mu$M. After stirring for 3 hours, the reaction mixture was extracted with dichloromethane, dried with sodium sulfate and concentrated with a rotary evaporator. The GC/mass spectral analysis of the concentrate extract showed complete conversion of the substrate to cinnamaldehyde ($C_6H_5$—CH=CH—CHO).

The reaction with the immobilized enzyme was carried out essentially in the same manner except that the catalyst is added as a suspension and the reaction mixture is heterogeneous. After the reaction, catalyst was simply filtered over Whatman filter paper and resuspended in buffer which is ready for reuse.

When and wherever side reactions were observed due to hydrogen peroxide (which is produced during the oxidation), 5 $\mu$l of catalase (1 mg/ml) was added to the reaction mixture prior to the addition of the catalyst as a hydrogen peroxide scavenger.

Reaction of 3-methyl-cyclopentanone

The reaction was carried out with both racemic and R-3-methyl-cyclopentanone, following the same experimental procedure as described above for a typical oxidation. The GC/MS analysis of the products for both the reactions indicated the formation of the products as show in scheme I. The racemic mixture formed two olefins and R-enantiomer formed exclusively one product. This clearly shows that the S-isomer, which has a hydrogen below the reaction plane forms, the substituted cyclopentenone whereas the R-enantiomer forms the unsubstituted olefin. As the S-enantiomer reacts faster than the R-enantiomer, this reaction is quite useful in the resolution of the substituted cyclopentanones.

Enantioselectivity And Resolution Of Racemic Carbonyl Compounds

Often biological activity is associated with only one enantiomer, sometime the other being undesirable with deleterious side effects. Moreover the optically pure compound may be more than twice as active as racemate. Although the abilities of enzymes to act as specific chiral catalysts due to the chirality of the active sites have been long recognized, its only recently that biocatalysts are employed in routine organic synthetic processes, particularly by the pharmaceutical industry. Using di-deuterated hydrocinnamaldehyde, it was demonstrated that the dehydrogenation is "trans" in forming the cinnamaldehyde. Also the reaction of the 8-CN-OYE with the 2- and 3-methyl substituted cyclopentanones established the regio- as well as the enantioselectivity of the reaction.

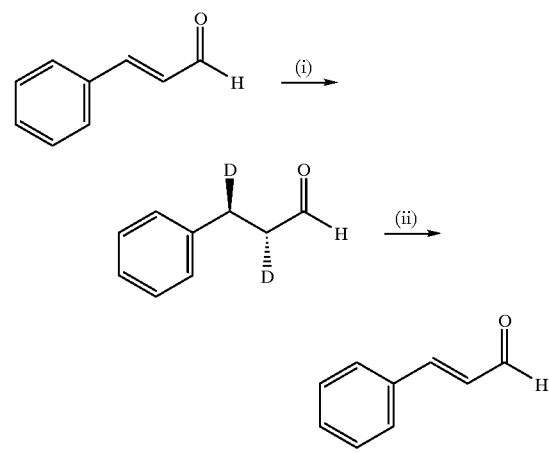

(i) native OYE, NaDPD, D$_2$O (ii) 8-CN-FMN-OYE, 100 mM KPi, pH 7

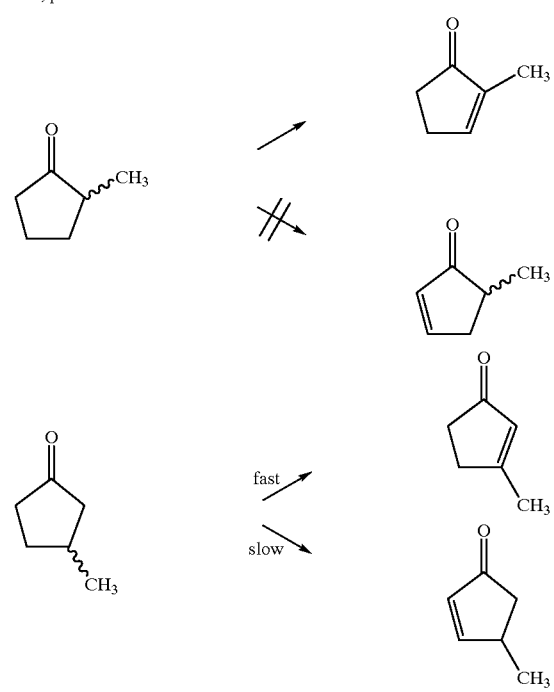

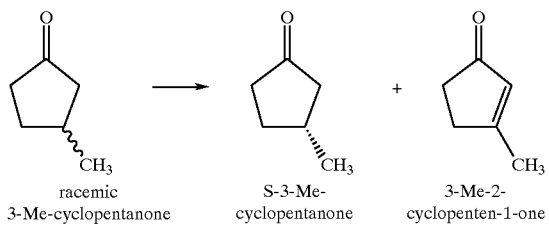

racemic 3-Me-cyclopentanone → S-3-Me-cyclopentanone + 3-Me-2-cyclopenten-1-one

Reaction with 3-phenyl-butyraldehyde

The racemic 3-phenyl-butyraldehyde was subjected to typical oxidation reaction with the catalytic system of the present invention. After prolonged reaction time (36 hours–48 hours), according to GC/MS, it was found that only ~50% substrate reacted to form the 4-phenyl-butenal. The rest of the reactant remained unaffected. It can be concluded, in analogy to the 3-Me-cyclopentanone reaction, that the oxidation of S-enantiomer only catalyzed by the catalyst leaving the R-enantiomer intact as hydrogen at the asymmetric center lies in unfavorable geometry. This reaction once again highlights the potential of the present catalytic system in resolving racemic carbonyl compounds.

Substrate Specificity

The process of the present invention can be used to resolve and convert 2-phenyl-propionaldehyde to phenyl acrylic acid in a one pot reaction. The enantioselective reduction of substituted acrylic acids is one of the industrial routes to make the anti-inflammatory, analgesic and anti-pyretic drugs like ibuprofen, ketoprofen, naproxen, etc. (Takakaya et al., Eur. Pat. Appl., 0 272 787, 1987). In the above reaction with 2-phenyl-propionaldehyde as substrate, the enzyme enantioselectively reacted with one of the optical isomers and converted it to the phenyl acraldehyde. This aldehyde was further oxidized to the acid, presumably by the hydrogen peroxide formed during the turn over. Such a side reaction can be prevented by incorporating bovine liver catalase in the reaction mixture.

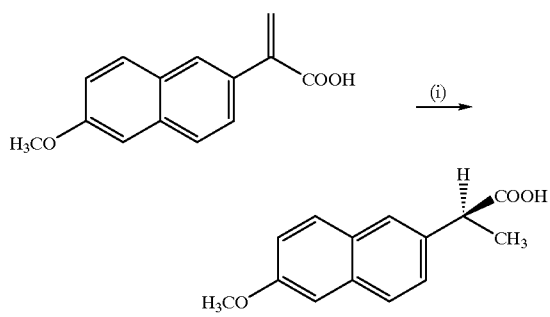

(i) enantiomerically pure ruthenium [2,2'-(diarylphosphino)-1,1'-binaphthyl] diacetate

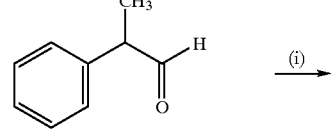

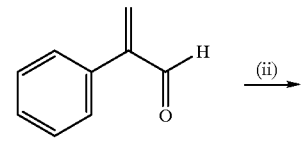

(i) 8-CN-FMN-OYE, 50 mM NaPi pH 8.5 (ii) $H_2O_2$

Immobilization of the 8-CN-FMN-OYE

One ml of 8-CN-FMN-OYE (~200 $\mu$M) in 0.1M phosphate buffer pH 7 was mixed with 2 $\mu$l of 0.1M p-Cl-phenol to obtain the green phenol-protein complex. 250 mg of 6-aminohexanoic acid N-hydroxysuccinimide ester-sepharose 4B (obtained from Sigma) was washed thoroughly with 40 ml of phosphate buffer over Whatman filter paper and obtained a wet pellet. The pellet was resuspended in 2 ml 0.1M phosphate buffer, pH 7. Then 1 ml of phenol-protein complex was mixed with the gel suspension and stirred at 4° C. with a small magnetic bar. After 3 hours, the gel was filtered over Whatman filter paper using Buchner funnel and the unreacted protein was washed off with 40 ml of buffer. The pellet was resuspended in 1 ml of 0.1M pyrophosphate buffer, pH 8.5 and is ready for use. The concentration of the catalysts was determined both by determining the unbound protein in the filtrate and also by the denaturation of the catalyst with 6N guanidine and measuring the concentration of the released cofactor.

The immobilized proteins were found to retain ~100% activity of the soluble proteins.

Catalytic Activity Of 8-CN-FMN-OYE

The reconstituted protein retained about 1% of the NADPH oxidase and NADPH- cyclohexenone reductase activity of the native enzyme. However it was found that the 8-CN-FMN-OYE catalyzed efficiently the oxidation of saturated carbonyl compounds with molecular oxygen as acceptor, as illustrated below:

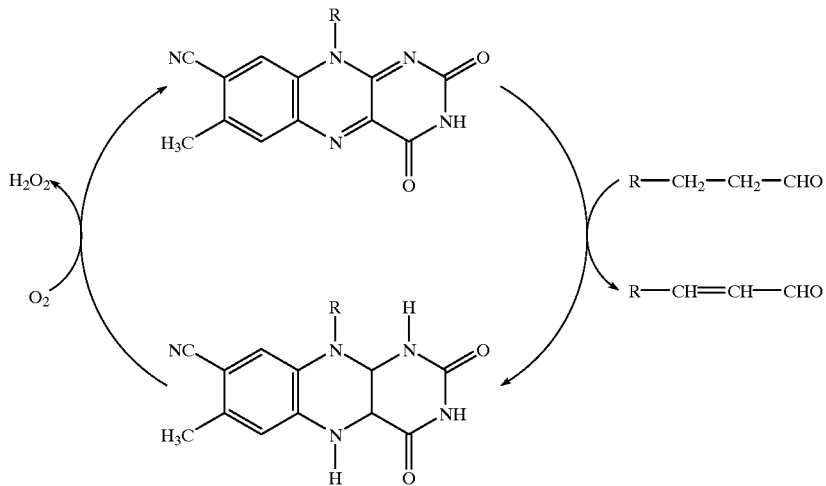

Having now fully described the invention, it will be apparent to one of ordinary skill in the art that many changes and modifications can be made thereto without departing from the spirit or scope of the invention.

TABLE 1

| | | |
|---|---|---|
| (1) | $CH_3—CH_2—CH_2—CHO$ | → $CH3—CH=CH—CHO$ |
| (2) | $CH_3—(CH_2)_5—CHO$ | → $CH_3—(CH_2)_3—CH=CH—CHO$ |
| (3) | $CH_3—(CH_2)_7—CHO$ | → $CH_3—(CH_2)_7—CH=CH—CHO$ |
| (4) | $CH_3—CO—CH_2—COA$ | → Reduction of bound flavin observed |
| (5) | $CH_3—(CH_2)_6—COA$ | → Reduction of bound flavin observed |
| (6) | $C_6H_5—CH_2—CH_2—CHO$ | → $C_6H_5—CH=CH—CHO$ |
| (7) | $C_6H_5—CH_2—CH_2—CO—CH_3$ | → $C_6H_5—CH=CH—CO—CH$ |
| (8) | $CH_3—CH(CH_3)—CH_2—CHO$ | → $CH_3—C(CH_3)=CH—CHO$ |
| (9) | $CH_3—CH_2—CO—CH_3$ | → $CH_2=CH—CO—CH_3$ |
| (10) | $CH_3—CH_2—CH(CH_3)—CHO$ | → $CH_3—CH=C(CH_3)—CHO$ |
| (11) | $CH_3—CH_2—CO—CH_2CH_3$ | → $CH_3—CH_2—CO—CH=CH_2$ |
| (12) | $CH_3—CO—CH(CH_3)—CH_2—CH_3$ | → $CH_3—CO—C(CH_3)=CH—CH_3$ |
| (13) | $C_6H_5—CO—CH_2—CH_2—CH_3$ | → $C_6H_5—CO—CH=CH—CH_3$ |
| (14) | $C_6H_5—N=N—CO—NH—NH—C_6H_5$ | → $C_6H_5—N=N—CO—N=N—C_6H_5$ |
| (15) | $C_6H_5—N=N—CS—NH—NH—C_6H_5$ | → $C_6H_5—N=N—CS—N=N—C_6H_5$ |
| (16) | oxazolidinone | → oxazolone |
| (17) | cyclopentanone | → cyclopentenone |

TABLE 1-continued
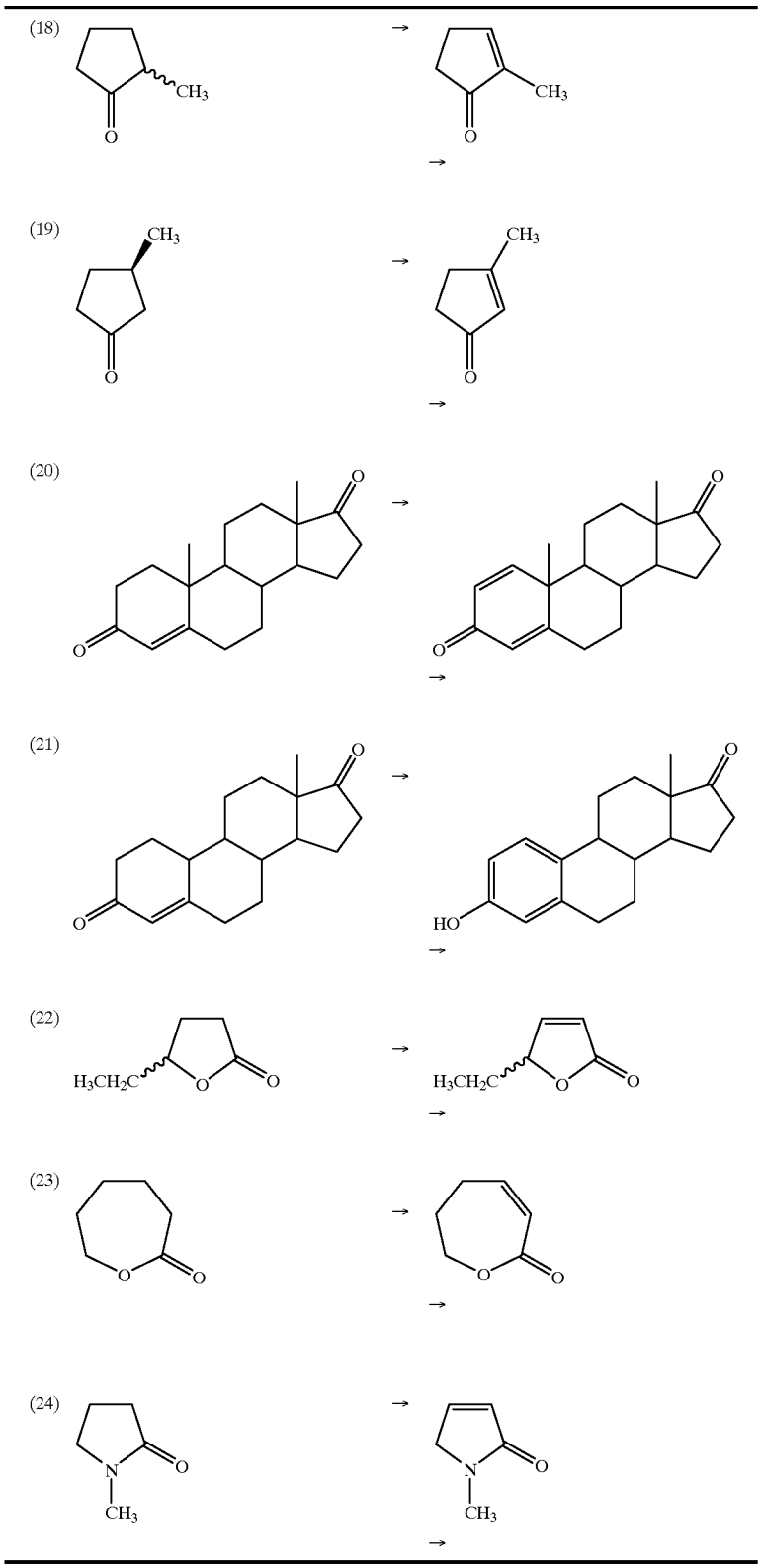

Oxidation of Racemic and R-3-methyl-cyclopentanone

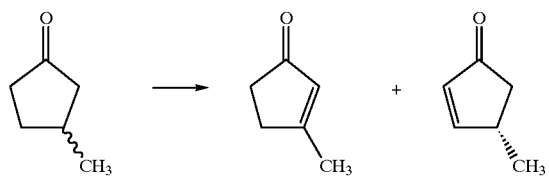

Racemic-3-Me-cyclopentanone

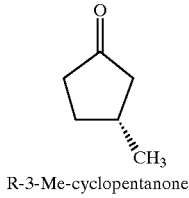

R-3-Me-cyclopentanone

Oxidation of 3-phenyl-bytyraldehyde

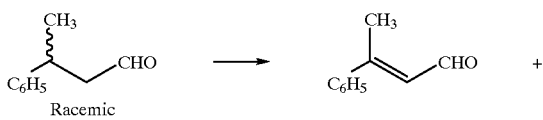

Racemic

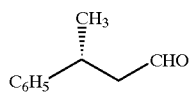

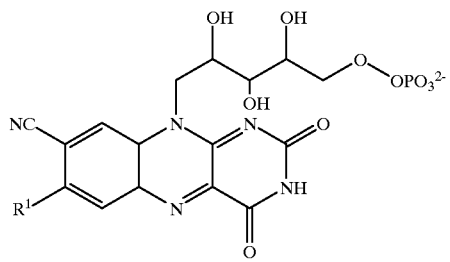

What is claimed is:

1. A compound of the formula:

2. The compound of claim 1, which is immobilized on a solid support.

3. The compound of claim 2, wherein said solid support is an insoluble polymer support.

4. The compound of claim 3, wherein the insoluble polymer support is 6-aminohexanoic acid N-hydroxysuccinimide ester-sepharose 4B.

5. The compound of claim 1, wherein $R^1$ is methyl.

* * * * *